US006445300B1

(12) United States Patent
Luman

(10) Patent No.: US 6,445,300 B1
(45) Date of Patent: Sep. 3, 2002

(54) PERSONAL EMERGENCY INFORMATION TRANSMITTER

(75) Inventor: David J. Luman, Meridian, ID (US)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/885,317

(22) Filed: Jun. 19, 2001

(51) Int. Cl.[7] ............................................... G08B 23/00
(52) U.S. Cl. ............................ 340/573.1; 340/573.4; 340/539; 340/286.07; 340/825.49
(58) Field of Search ........................ 340/573.1, 573.4, 340/539, 286.07, 286.06, 825.08, 825.49; 128/903, 904; 455/66, 100, 524

(56) References Cited

U.S. PATENT DOCUMENTS

| | | | |
|---|---|---|---|
| 3,828,306 A | 8/1974 | Angeloni | 340/32 |
| 4,764,757 A | 8/1988 | DeMarco et al. | 340/574 |
| 4,777,658 A | 10/1988 | Wren | 455/260 |
| 4,908,602 A | 3/1990 | Reich et al. | 340/514 |
| 5,438,607 A | 8/1995 | Przygoda, Jr. et al. | 379/38 |
| 5,465,082 A | * 11/1995 | Chaco | 340/573.1 |
| 5,745,033 A | 4/1998 | Jenkins, Jr. et al. | 340/539 |
| 5,874,897 A | * 2/1999 | Klempau | 340/573.1 |
| 5,877,675 A | * 3/1999 | Rebstock | 340/286.07 |
| 5,936,529 A | * 8/1999 | Reisman | 340/573.1 |
| 6,028,514 A | * 2/2000 | Lemelson | 340/539 |
| 6,084,525 A | 7/2000 | Toyota et al. | 340/690 |

* cited by examiner

Primary Examiner—Anh V La
(74) Attorney, Agent, or Firm—James R. McDaniel

(57) ABSTRACT

This invention relates to a small, wireless transmitter which contains important, personal information, such as the user's name, address, current medications, allergies, contact information or the like. When the user gets into trouble or becomes incapacitated, the transmitter could be used to send a signal to emergency response personnel. In this manner, emergency response personnel could respond to the distress signal and assist the user.

10 Claims, 4 Drawing Sheets

PERSONAL EMERGENCY INFORMATION TRANSMITTER

FIELD OF THE INVENTION

This invention relates to a small, wireless transmitter which contains important, personal information, such as the user's name, address, current medications, allergies, contact information or the like. When the user gets into trouble or becomes incapacitated, the transmitter could be used to send a signal to emergency response personnel. In this manner, emergency response personnel could respond to the distress signal and assist the user.

DESCRIPTION OF THE RELATED ART

Prior to the present invention, as set forth in general terms above and more specifically below, it is known in emergency signaling devices to employ remote transmitters. Exemplary of such prior art is U.S. Pat. No. 6,084,525 ('525) to K. Toyota et al., entitled "Distress Call Emitting Device." While the '525 reference employs a remote transmitter which is used to sense earthquakes and allow emergency response personnel to locate the user if the user is trapped under debris caused by earthquake, a more advantageous transmitter, then, would be presented if the transmitter could also supply personal information about the user.

It is also known in emergency signaling devices to provide information about the emergency. Exemplary of such prior art is U.S. Pat. No. 5,438,607 ('607) to C.T. Przygoda, Jr. et al., entitled "Programmable Monitoring System and Method." While the '607 reference teaches a monitoring system in which information about the nature of the emergency, such as fire, medical, low transmitter battery or the like can be transmitted, this information must be transmitted to a central monitoring system. Consequently, a further advantageous transmitter, then, would be presented if the transmitter could be used anywhere.

It is apparent from the above that there exists a need in the art for a transmitter which is lightweight and portable through simplicity of parts and uniqueness of structure, and which is capable of a sending an emergency distress signal, but which at the same time can be used anywhere and provide vital, personal information about the user to the emergency response personnel. It is a purpose of this invention to fulfill this and other needs in the art in a manner more apparent to the skilled artisan once given the following disclosure.

SUMMARY OF THE INVENTION

Generally speaking, this invention fulfills these needs by providing an emergency distress response method, comprising the steps of: downloading of personal information by a user into a transmitter; encountering a distress situation by said user; transmitting a signal by said transmitter; interacting with said transmitter by emergency personnel; downloading a first portion of said personal information by said emergency personnel; determining if said first portion of personal information is adequate; and downloading, if necessary, a second portion of said personal information.

In certain preferred embodiments, the first portion of the personal information may be, but is not limited to, the first name of the user and the city, state, and country where the user resides. Also, the second portion of the personal information can be, but is not limited to, more vital, personal information of the user, such as the user's full name, home address, contact person(s), medical condition, current medications, allergies, preferred medical provider, physician, social security number, home telephone number or anything that may possibly be needed by the emergency response personnel in case the user becomes distressed or incapacitated. Also, the personal information is downloaded into the transmitter through the use of a conventional information inputting device, such as a personal computer. Finally, the method also includes the step of determining if the user is from out-of-state.

In another preferred embodiment, the transmitter allows the emergency response personnel to interact with the user in order to obtain varying degrees of personal information about the user without having to move the user, if the user is incapacitated.

The preferred transmitter, according to this invention, offers the following advantages: lightness in weight; excellent distress signaling characteristics; excellent personal information storage characteristics; excellent personal information retrieval characteristics; portability; good durability; good stability; excellent economy; and ease-of-use. In fact, in many of the preferred embodiments, these factors of distress signaling characteristics, personal information storage characteristics, personal information retrieval characteristics, portability, economy, and ease-of-use are optimized to an extent that is considerably higher than heretofore achieved in prior, known transmitters.

The above and other features of the present invention, which will become more apparent as description proceeds, are best understood by considering the following detailed description in conjunction with the accompanying drawings, wherein like characters represent like parts throughout the several views and in which:

DETAILED DESCRIPTION OF THE INVENTION

Figure 1:
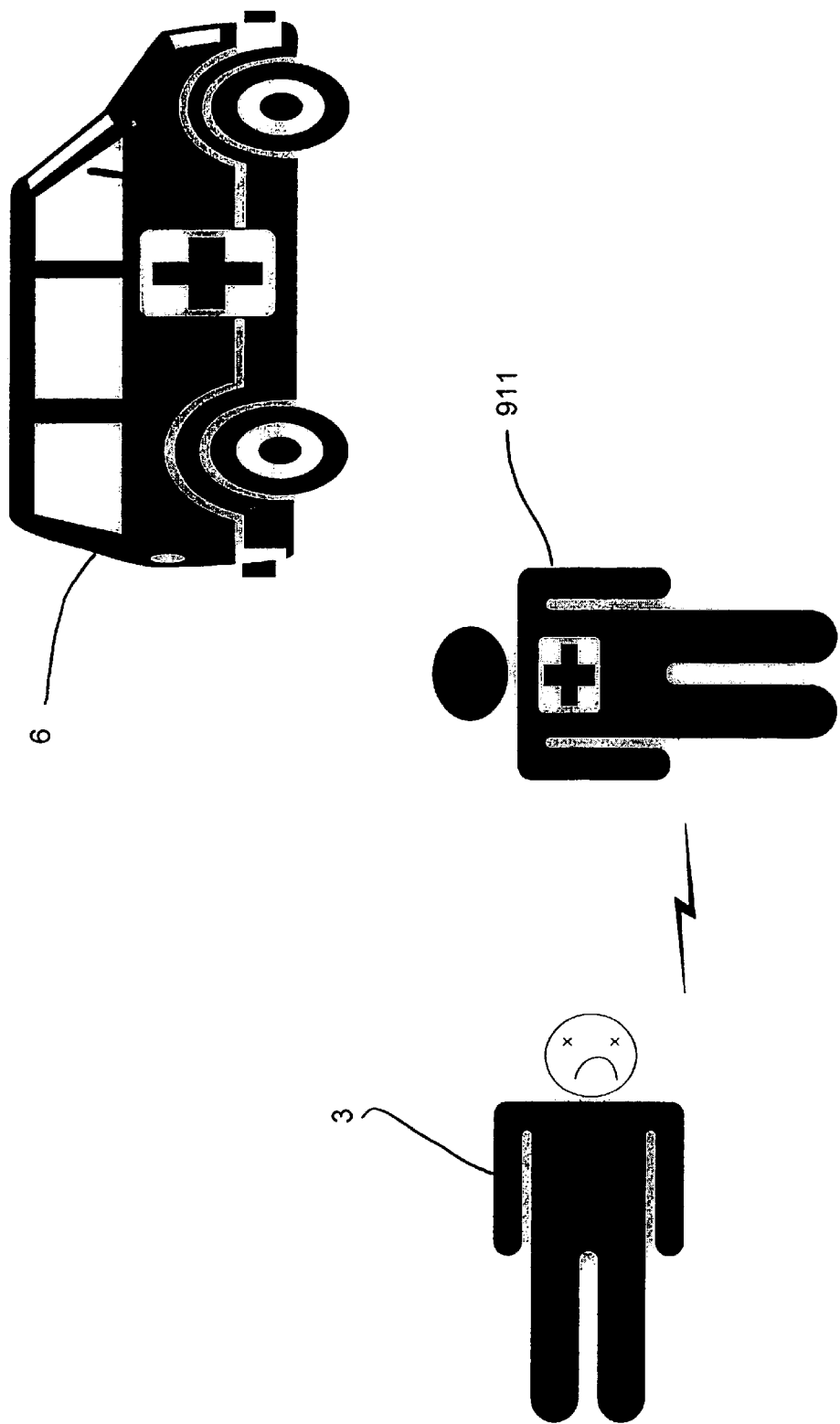
FIG. 1 is a schematic illustration of an emergency response personnel attending to an incapacitated user, according to one embodiment of the present invention.

With reference first to FIG. 1, there is illustrated one preferred embodiment for use of the concepts of this invention. As can be seen in FIG. 1, user 3 has become incapacitated and has signaled emergency response personnel 911. Emergency response personnel 911, such as paramedics, police or the like, have arrived at the scene in a conventional emergency response vehicle 6, such as an ambulance or a police car. Emergency response personnel 911 wirelessly interact with incapacitated user 3 in order to obtain a variety of vital information about user 3. The type of information available regarding user 3 will be discussed in detailed later.

Figure 2:
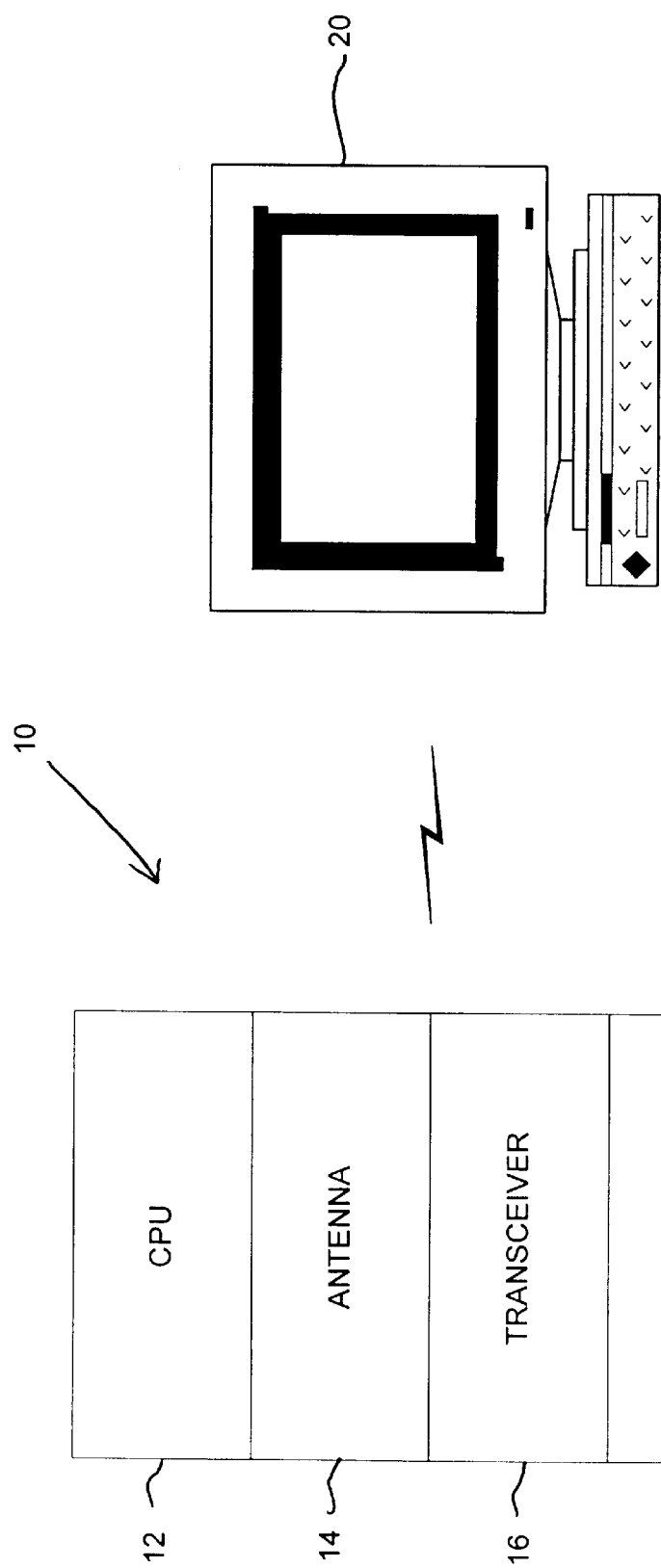
FIG. 2 is a schematic illustration of downloading to the transmitter from the information inputting device.

FIG. 2 of illustrates transmitter 10 and conventional information inputting device 20. Transmitter 10, preferably, includes, in part, central processing unit (CPU) 12, antenna 14, transceiver 16, and storage memory 18. It is to the understood that transmitter 10 should be small, lightweight, portable, and inexpensive. It is also be desired that transmitter 10 be inconspicuous to carry around, such as, but not limited to, an identification card, key fob or the like. Finally, it is to be understood that an optional global positioning system (GPS) 19 could be added to transmitter 10 in order to further assist emergency response personnel 911 in locating user 3, especially if user 3 becomes incapacitated.

As shown in FIG. 2, personal information about user 3 is entered into information inputting device 20 and then transmitted to transmitter 10. It is to be understood that the information entered into transmitter 10 can be entered wirelessly through the use of conventional connection protocols.

With respect to the information entered by user 3 into information inputting device 20 and then into transmitter 10, a variety of vital, personal information can be downloaded into transmitter 10. Such personal information about user 3 can be, but is not limited to, user's full name, user's home address, contact person(s), user's medical condition, user's allergies, user's preferred medical provider, user's physician, user's social security number, user's blood type, if user 3 is an organ donor, do not resuscitate requests by user 3, user's home telephone number or anything possibly needed by emergency response personnel 911 in case user 3 encounters any type of distress or emergency.

It is also to be understood that user 3 can enter two levels of personal information into transmitter 10. The first level being, for example, the first name of user 3, contact person(s) and the city, state, and country where user 3 resides. The second level being, for example, some or all of the other personal information listed above. In this manner, if, for example, user 3 is merely lost, emergency response personnel 911 need only to review this first level of personal information of user 3 in order to assist user 3 in getting back home. Otherwise, if user 3 is incapacitated, emergency response personnel 911 may need to review the first and second levels of personal information of user 3 in order to assist user 3. It is to be understood that user 3 can enter whatever information user 3 deems appropriate in whatever level user 3 deems appropriate.

Figure 3:
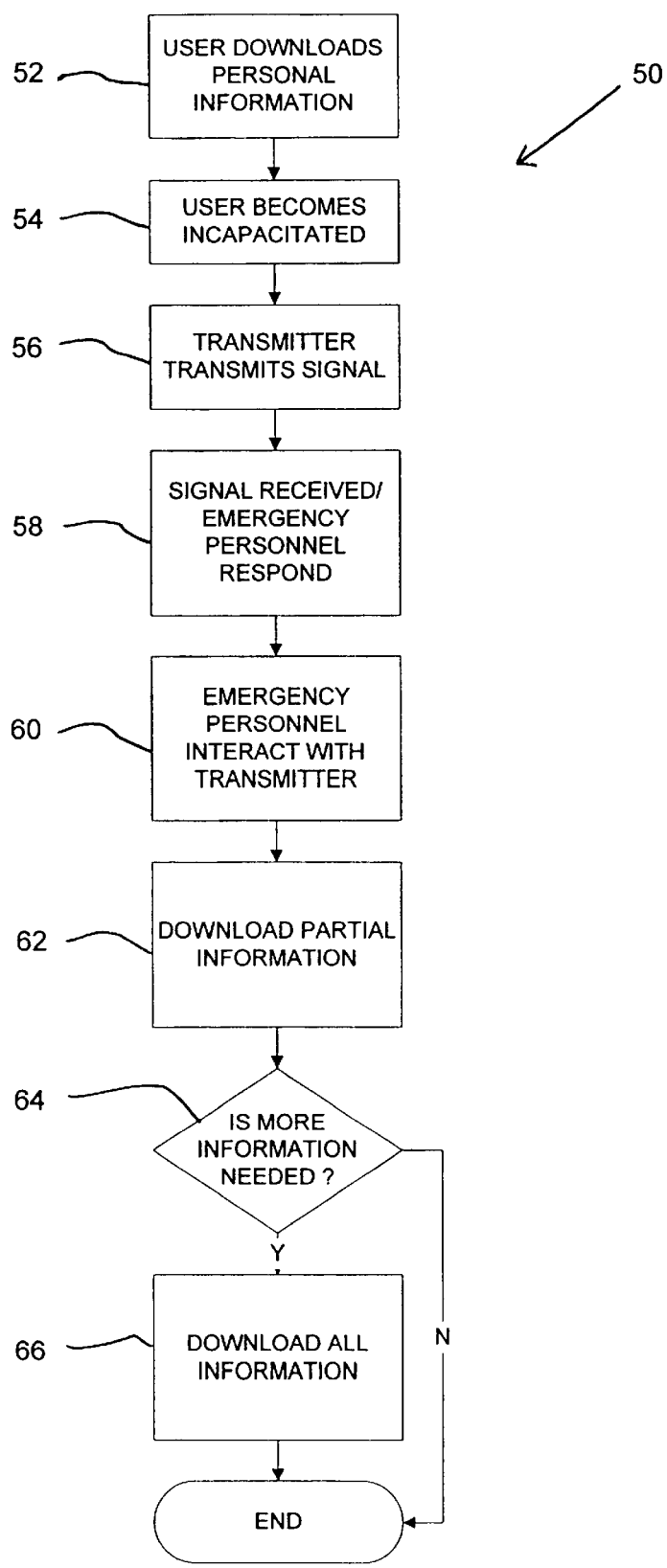
FIG. 3 is a flowchart that illustrates a method of responding to an incapacitated user by personal emergency, according to another embodiment of the present invention.

With respect to FIG. 3, there is illustrated emergency distress response method 50. Method 50 includes, in part, the steps of: user 3 downloading personal information (step 52); user 3 becoming incapacitated (step 54); transmitter 10 transmitting the signal (step 56); signal received/emergency response personnel 911 respond (step 58); emergency response personnel 911 interact with transmitter 10 (step 60); emergency personnel 911 download partial information (step 62); determining if more information regarding user 3 is needed (step 64); and downloading all personal information of user 3 (step 66).

As discussed above with respect to step 52, there are two levels of information that user 3 can enter into transmitter 10. In this regard, the first level is conventionally encrypted with a public key so that this information can be easily accessed by emergency response personnel 911. In this manner, this first level of information is always available because transmitter 10 should always be active. If emergency response personnel 911 require further detailed information on user 3, emergency response personnel 911 must be able to access the second level of personal information about user 3. This is accomplished by conventionally encrypting the second level of personal information of user 3 with a private key that can only be accessed by qualified emergency response personnel 911. Emergency response personnel 911 need only to activate the private key in order to gain access to this second level of personal information of user 3.

With respect to step 54, once the user 3 has become incapacitated, transmitter 10 begins to sound out an audible sound through transceiver 16. It is also to be understood that transmitter 10 can also vibrate or produce any suitable alarm/alert. Transmitter 10 continues to send out the alarm at increasingly louder/higher levels until user 3 de-activates the alarm/alert mechanism. If user 3 is incapacitated, user 3 probably will not be able to deactivate the alarm/alert mechanism, and after a predetermined period of time, for example, 60 seconds, transmitter 10 broadcasts a need for assistance, as shown in step 56. It is to be understood that transmitter 10 may contact emergency response personnel 911 wirelessly through the connection protocols described above, if optional GPS 19 is installed. Emergency response personnel 911 receive the transmitted distress signal and determine where user 911 is according to GPS 19 in transmitter 10. It is to be further understood that the transmitted distress-signal can be received by emergency response personnel 911 through any suitable device, such as a personal digital assistant (PDA), personal computer (PC) or the like.

Once emergency response personnel 911 have arrived at the scene where user 3 is incapacitated, emergency response personnel 911 can conventionally download information regarding user 3 from transmitter 10 through the use of the suitable devices discussed above, such as a PDA or PC. This allows emergency response personnel 911 to interact with user 3 without having to move user 3. As discussed above, emergency response personnel 911 can have access to two levels of personal information regarding user 3, depending upon the type of distress/emergency experienced by user 3. If the first level of information regarding user 3 is adequate, then emergency response personnel 911 do not need to review the second level of information, as shown in step 64. However, if user 3 is incapacitated, emergency response personnel 911 may need to review this second level of information by using the private key, as shown in step 66.

Figure 4:
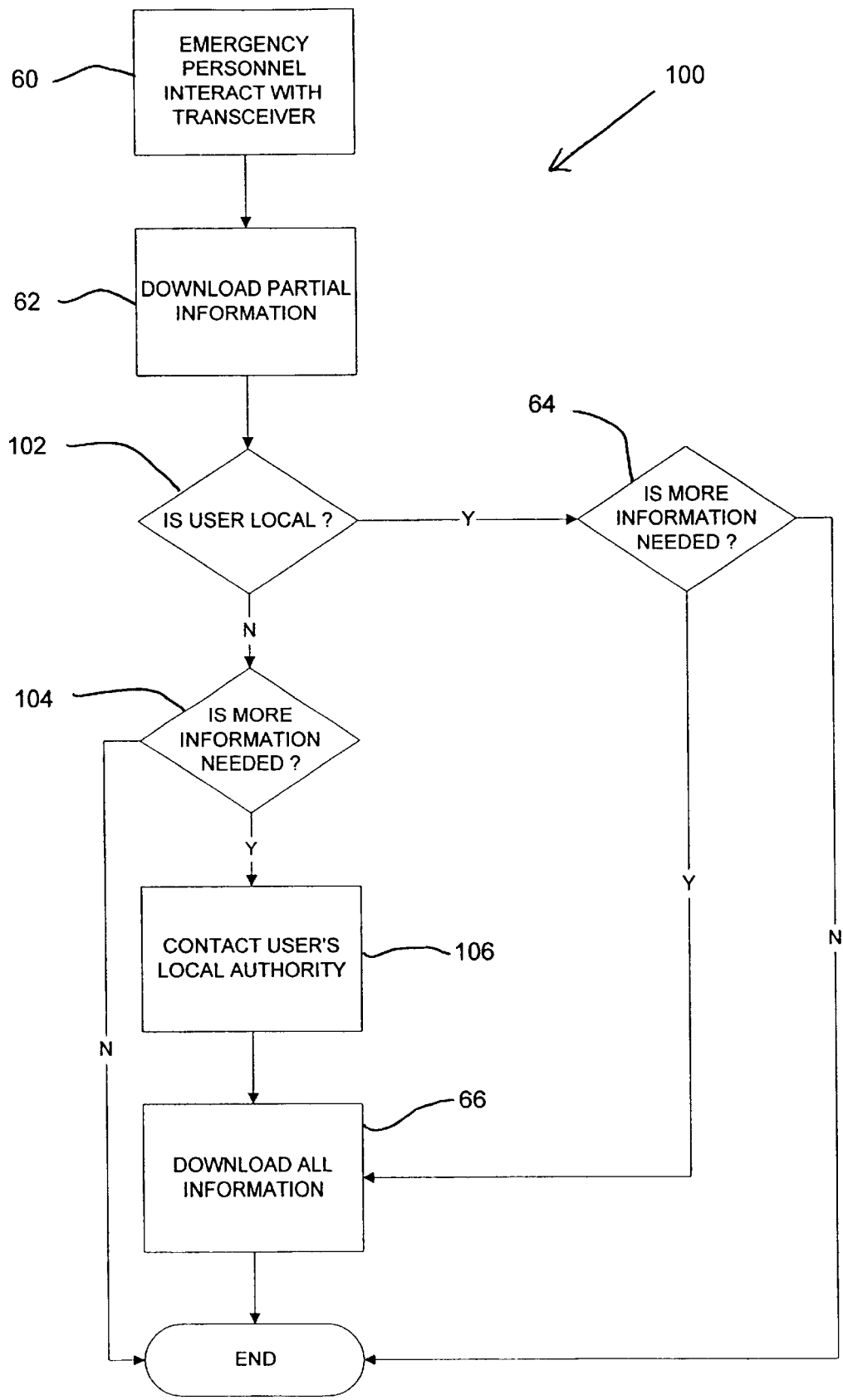
FIG. 4 is a flowchart that illustrates another method of responding to an incapacitated user by personal emergency, according to still another embodiment of the present invention.

FIG. 4 illustrates another emergency distress response method 100. Method 100 is utilized to determine if user 3 is from out-of-town. Method 100 includes, in part, the steps of: emergency response personnel 911 interacting with transmitter 10 (step 60); downloading partial information (step 62); determining if user 3 is a local (step 102); determining if more information about user 3 is needed (step 104); contacting the user's local authority (step 106); downloading all information (step 66); and determining if more information is needed if user 3 is a local (step 64).

With respect to step 102, emergency response personnel 911 can review the first level of personal information of user 3 in order to determine if user 3 is from out-of-town. If user 3 is from out-of-town, emergency response personnel 911 can determine if more personal information is needed regarding user 3, as shown in step 104. If more personal information is needed then emergency response personnel 911 can contact the user's local authority, such as a county paramedic unit or city hospital located in/near the user's residence by contacting the local authority based upon the user's city, state and country residence, as shown in step 106. As discussed above, this general residence information can be located on the first level of the user's personal information. Once the user's local authority has been contacted, the user's local authority can then provide emergency response personnel 911 with the private key, as discussed above, so that emergency response personnel 911 can access the second level of personal information of user 3.

If it is determined that user 3 is a local, then emergency response personnel 911 can determine if more information is needed, as discussed above with respect to step 64.

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. An emergency distress response method, comprising the steps of:

downloading of a first and a second portions of personal information by a user into a transmitter;

encrypting said first portion of said personal information with a public key;

encrypting said second portion of said personal information with a private key;

encountering a distress/emergency situation by said user;

transmitting a signal by said transmitter;

interacting with said transmitter by emergency personnel;

downloading said first portion of said personal information by said emergency personnel;

determining if said first portion of personal information is adequate;

downloading, if necessary, said second portion of said personal information;

determining if said user is from out-of-town; and contacting, if necessary, a user's local authority.

2. The method, as in claim 1, wherein said transmitting step is further comprised of the step of:

wirelessly transmitting said signal.

3. The method, as in claim 1, wherein said first portion is further comprised of:

the user's name; and the user's city, state, and country residence.

4. The method, as in claim 1, wherein said transmitting step is further comprised of steps of:

activating an alarm/alert system located substantially within said transmitter;

transmitting said signal if said user does not de-activate said alarm/alert system within a predetermined amount time.

5. The method, as in claim 1, wherein said downloading personal information step is further comprised of the step of:

wirelessly downloading said personal information from an information inputting device into said transmitter.

6. An out-of-town/local determination/emergency distress response method, comprising the steps of:

downloading of a first and second portions of personal information by a user into a transmitter;

encrypting said first portion of said personal information with a public key;

encrypting said second portion of said personal information with a private key;

encountering a distress/emergency situation by said user;

transmitting a signal by said transmitter;

interacting with said transmitter by emergency personnel;

downloading said first portion of said personal information by said emergency personnel;

determining if said first portion of personal information is adequate;

determining if said user is from out-of-town;

contacting, if necessary, a user's local authority; and downloading, if necessary, said second portion of said personal information.

7. The method, as in claim 6, wherein said transmitting step is further comprised of the step of:

wirelessly transmitting said signal.

8. The method, as in claim 6, wherein said first portion is further comprised of:

the user's name; and the user's city, state, and country residence.

9. The method, as in claim 6, wherein said transmitting step is further comprised of steps of:

activating an alarm/alert system located substantially within said transmitter;

transmitting said signal if said user does not de-activate said alarm/alert system within a predetermined amount time.

10. The method, as in claim 6, wherein said downloading personal information step is further comprised of the step of:

wirelessly downloading said personal information from an information inputting device into said transmitter.

* * * * *